United States Patent
Kopf-Sill

(10) Patent No.: US 6,221,226 B1
(45) Date of Patent: Apr. 24, 2001

(54) METHODS AND SYSTEMS FOR MONITORING AND CONTROLLING FLUID FLOW RATES IN MICROFLUIDIC SYSTEMS

(75) Inventor: Anne R. Kopf-Sill, Portola Valley, CA (US)

(73) Assignee: Caliper Technologies Corp., Mountain View, CA (US)

(*) Notice: Subject to any disclaimer, the term of this patent is extended or adjusted under 35 U.S.C. 154(b) by 0 days.

(21) Appl. No.: 09/413,961

(22) Filed: Oct. 7, 1999

Related U.S. Application Data

(63) Continuation of application No. 08/895,058, filed on Jul. 15, 1997, now Pat. No. 6,001,231.

(51) Int. Cl.$^7$ .................................................... G01N 27/26
(52) U.S. Cl. .......................... 204/602; 204/452; 204/454; 422/110; 422/70
(58) Field of Search .................................... 204/452, 454, 204/602; 422/70, 110, 50; 210/656

(56) References Cited

U.S. PATENT DOCUMENTS

| | | |
|---|---|---|
| 4,675,300 | 6/1987 | Zare et al. . |
| 4,908,112 | 3/1990 | Pace . |
| 5,006,473 | 4/1991 | Bouma et al. . |
| 5,126,022 | 6/1992 | Soane et al. . |

(List continued on next page.)

FOREIGN PATENT DOCUMENTS

| | | |
|---|---|---|
| WO 9604547 | 2/1996 | (WO) . |
| WO 9800231 | 1/1998 | (WO) . |
| WO 9800705 | 1/1998 | (WO) . |
| WO 9800707 | 1/1998 | (WO) . |
| WO 9805424 | 2/1998 | (WO) . |

OTHER PUBLICATIONS

Hayes et al. ("Electroosmotic Flow Control and Monitoring with an Applied Radial Voltage for Capillary Zone Electrophoresis", Anal. Chem. 1992, 64, 512–516), Mar. 1992.*

Crowley, J.M. et al., "Selecting a Working Fluid to Increase the Efficiency and Flow Rate of an EHD Pump," *IEEE Transactions on Industry Applications* 26(1) Jan./Feb., 42–49.

Dasgupta, P.K. et al., "Electroosmosis: A Reliable Fluid Propulsion System for Flow Injection Analysis," *Anal. Chem.* 66:1792–1798 (1994) 7.

Hlatshwayo, A.B., "Analytical separation of colloidal particles using capillary electrophoresis," Book of abstracts, 212$^{th}$ ACS National Meeting, Orlando, FL (Aug. 25–29, 1996).

Lee, T.T. et al., "Real–Time Measurement of Electroosmotic Flow in Capillary Zone Electrophoresis," *Anal. Chem.* 66(17):2694–2700 (1994) Sep.

Manz, A. et al., "Electroosmotic pumping and electrophoretic separations for miniaturized chemical analysis systems," *J. Micromech. Microeng.* 4:257–265 (1994)7.

Ramsey, J.M. et al., "Microfabricated chemical measurement systems," *Nature Med.* 1:1093–1096 (1995) Oct.

Seiler, K. et al., "Electroosmotic Pumping and Valveless Control of Fluid Flow Within a Manifold of Capillaries on a Glass Chip," *Anal. Chem.* 66:3485–3491 (1994) Oct.

*Primary Examiner*—T. Tung
*Assistant Examiner*—Alex Noguerola
(74) *Attorney, Agent, or Firm*—Matthew B. Murphy

(57) ABSTRACT

The present invention generally provides methods and systems for monitoring and controlling electroosmotic flow rates in microfluidic systems. Generally, such methods and systems monitor flow rates in electroosmotically driven microfluidic systems by flowing signaling elements within these channels and measuring the flow rate of these signals. The methods of monitoring flow rates are also applied to methods and systems for continuously monitoring and controlling these flow rates in electroosmotically driven microfluidic systems.

22 Claims, 5 Drawing Sheets

U.S. PATENT DOCUMENTS

| | | |
|---|---|---|
| 5,286,356 | 2/1994 | Jones et al. . |
| 5,296,116 | 3/1994 | Guttman . |
| 5,302,264 * | 4/1994 | Welch et al. ................. 204/452 |
| 5,498,324 | 3/1996 | Yeung et al. . |
| 5,571,410 | 11/1996 | Swedberg et al. . |
| 5,585,069 | 12/1996 | Zanzucchi et al. . |
| 5,593,838 | 1/1997 | Zanzucchi et al. . |
| 5,603,351 * | 2/1997 | Cherukuri et al. ............ 137/597 |
| 5,605,662 | 2/1997 | Heller et al. . |
| 5,630,924 * | 5/1997 | Fuchs et al. .................. 204/601 |
| 5,643,738 | 7/1997 | Zanzucchi et al. . |
| 5,858,187 * | 1/1999 | Ramsey et al. ............... 204/452 |

* cited by examiner

METHODS AND SYSTEMS FOR MONITORING AND CONTROLLING FLUID FLOW RATES IN MICROFLUIDIC SYSTEMS

CROSS-REFERENCE TO RELATED APPLICATION

This application is a continuation of USSN 08/895,058, filed Jul. 15, 1997, now U.S. Pat. No. 6,001,231.

BACKGROUND OF THE INVENTION

Microfluidic systems have been gaining increasing interest for use in chemical and biochemical analysis and synthesis. Miniaturization of a variety of laboratory analyses provides myriad benefits, including providing substantial savings in time of analysis, cost of analysis, and space requirements for the equipment which performs this analysis. Another touted advantage of microfluidic systems is their suggested adaptability as automated systems, thereby providing additional savings associated with the costs of the human factor of performing analyses, e.g., labor costs, costs associated with operator error, and generalized costs associated with the imperfection of human operations, generally.

A number of different microfluidic technologies have been proposed for realizing the potential of these systems. For example, microfluidic systems have been proposed that are based upon microscale channels or conduits through which fluid is transported by internal or external pressure sources, e.g., pressure pumps, and wherein fluid direction, e.g., as between two potential fluid paths, is carried out using microfabricated mechanical valve structures. Other unrealized technologies have proposed utilizing acoustic energy, or electrohydrodynamic pumping of fluids to effect fluid movement. However, due to fundamental problems with these technologies, e.g., excessive costs or inoperability, they have largely floundered in the research institutions where they were originally conceived.

Electrokinetic material transport systems have shown the ability to fulfill the promise of microfluidics by providing an accurate, automatable, easily manufacturable system for manipulating fluids within microscale systems. Despite the advances of electrokinetic flow systems, it would generally be desirable to provide more and more complex systems for performing a wide variety of different fluidic operations, integrating multiple operations in a single microfluidic system, as well as provide systems capable of performing massively parallel experimentation. In order to provide such systems, it would generally be desirable to provide such systems with advanced abilities to monitor and control the relevant parameters of any and all fluidic elements within a given system, including variables such as temperature, time of reaction, length of separations, and the like. The present invention provides methods and systems that meet these and other needs by providing an operator with greater ability to monitor and control microfluidic systems.

SUMMARY OF THE INVENTION

The present invention is generally directed to methods and systems utilized in monitoring and controlling flow rates within microfluidic channel systems. As such, in a first aspect, the present invention provides a method of monitoring an electroosmotic flow rate of fluid in a microfluidic device having at least first and second intersecting microscale-channels disposed therein. The method comprises flowing a fluid along the first channel by applying a voltage gradient across a length of the first channel. A detectable amount of a signaling compound is then injected into the first channel. The flow rate of fluid in the first channel is then determined from the rate at which the signaling compound flows from a first point in the first channel to a second point in the first channel. This is repeated in a second channel. Specifically, a fluid is also flowed along the second channel by applying a voltage gradient across a length of the second channel, a detectable amount of a signaling compound is injected into the second channel, and the flow rate of fluid in the second channel is determined from the rate at which the signaling compound flows from a first point in the second channel to a second point in the second channel.

In an alternate embodiment, the present invention provides a microfluidic system employing at least first and second intersecting microscale channels disposed in a body structure, wherein the system is used for analyzing a result of a chemical reaction which produces a first detectable signal. In particular, the present invention provides a method of monitoring a flow rate of a fluid in the first channel, which comprises flowing a fluid in the first channel and injecting into the first channel, a detectable amount of a signaling compound. In this aspect, the signaling compound produces a second detectable signal that is capable of being distinguished from the first detectable signal. The second detectable signal is then detected and distinguished from the first detectable signal. The flow rate of fluid in the main channel is then calculated from the amount of time between the injecting step and the detecting step.

In still another aspect, the present invention provides methods of continuously monitoring electroosmotic flow rate of a fluid in a microscale channel of a microfluidic device having at least first and second intersecting microscale channels disposed therein. The method comprises electroosmotically flowing the fluid along the first channel by applying a voltage gradient across the length of the first channel. A detectable amount of a signaling compound is periodically injected into the first channel at a first point. The periodic signal from the signaling compound is then detected at a second point in the first channel, the second point being removed from the first point. Variation in flow rate is then identified from a variation in the periodic signal detected in the detecting step.

In an additional aspect, the present invention provides a microfluidic device for use in accordance with the monitoring methods described herein. In particular, the device comprises a body structure having at least first, second and third channels disposed therein. The first channel comprises first and second reservoirs in fluid communication with its first and second termini. The first reservoir has the fluid deposited therein. The second channel intersects the first channel at a first terminus of the second channel, and has a third reservoir in fluid communication with a second terminus of the second channel. The third reservoir has a signaling compound disposed therein, which signaling compound is capable of producing a detectable signal. The third channel intersects the first channel at a first terminus of the third channel and has a fourth reservoir in fluid communication with a second terminus of the third channel. The device also comprises a detection window disposed across at least one of the first and second microscale channels, wherein the detection window is capable of transmitting the detectable signal therethrough.

The monitoring methods described herein are also useful in methods of controlling the electroosmotic flow rate of a fluid in a microfluidic device having at least a first microscale channel disposed therein. In particular, an electroosmotic flow rate is controlled by a method which comprises flowing the fluid along the first channel by applying a voltage gradient across a length of the first channel. A detectable amount of a signaling compound is injected into the first channel at a first point in the first channel. The actual flow rate of fluid is then determined from the rate at which the signaling compound flows along the first channel. The actual flow rate is then compared to a desired flow rate. The voltage gradient applied across the length of the first channel is then increased or decreased until the actual flow rate is approximately equal to the desired flow rate.

In a related aspect, the present invention provides a system for controlling an electroosmotic flow rate of a fluid in a microfluidic system. The system comprises a microfluidic device comprising at least first, second and third channels disposed therein, the first channel having first and second reservoirs in fluid communication with its first and second termini, the first reservoir having the fluid deposited therein, the second channel intersecting the first channel at a first terminus of the second channel, and having a third reservoir in fluid communication with a second terminus of the second channel the third reservoir having a signaling compound disposed therein, the third channel intersecting the first channel at a first terminus of the third channel, and having a fourth reservoir in fluid communication with a second terminus of the third channel. The system also comprises an electrical controller for concomitantly applying and modulating voltages at at least three of the first, second, third and fourth reservoirs, to flow a fluid in the first channel from the first reservoir to the second reservoir, and periodically injecting a detectable amount of the signaling compound into the first channel from the third reservoir. The system further includes a detector disposed adjacent to and in sensory communication with a point in the first channel, whereby the detector is capable of detecting the signaling compound at the first point in the first channel. In addition, the system comprises an appropriately programmed computer for receiving signal data from the detector, calculating the actual flow rate of the fluid in the channel from the signal data, comparing the actual flow rate, and instructing the electrical controller to increase or decrease the voltage gradient across the channel based upon a difference between the actual flow rate and the desired flow rate.

In still another aspect, the present invention provides a computer or processor for use in accordance with the monitoring and controlling methods and systems described herein. The computer or processor comprises appropriate programming for determining an actual electroosmotic flow rate of a fluid in a first microscale channel. The computer then compares the actual electroosmotic flow rate to a desired electroosmotic flow rate in the first microscale channel, and increases or decreases the voltage gradient applied across the first microscale channel depending upon the comparison of the actual electroosmotic flow rate to the desired electroosmotic flow rate, until the actual electroosmotic flow rate is approximately equal to the desired electroosmotic flow rate.

DETAILED DESCRIPTION OF THE INVENTION

I. General

Microfluidic systems have been described for use in the performance of a large number of useful operations. Of increasing interest is the use of such systems in the performance of wide varieties of chemical and biochemical reactions, including analytical and synthetic reactions.

As used herein, the term "microscale" or "microfabricated" generally refers to structural elements or features of a device which have at least one fabricated dimension in the range of from about 0.1 $\mu$m to about 500 $\mu$m. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 5 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

Figure 1:
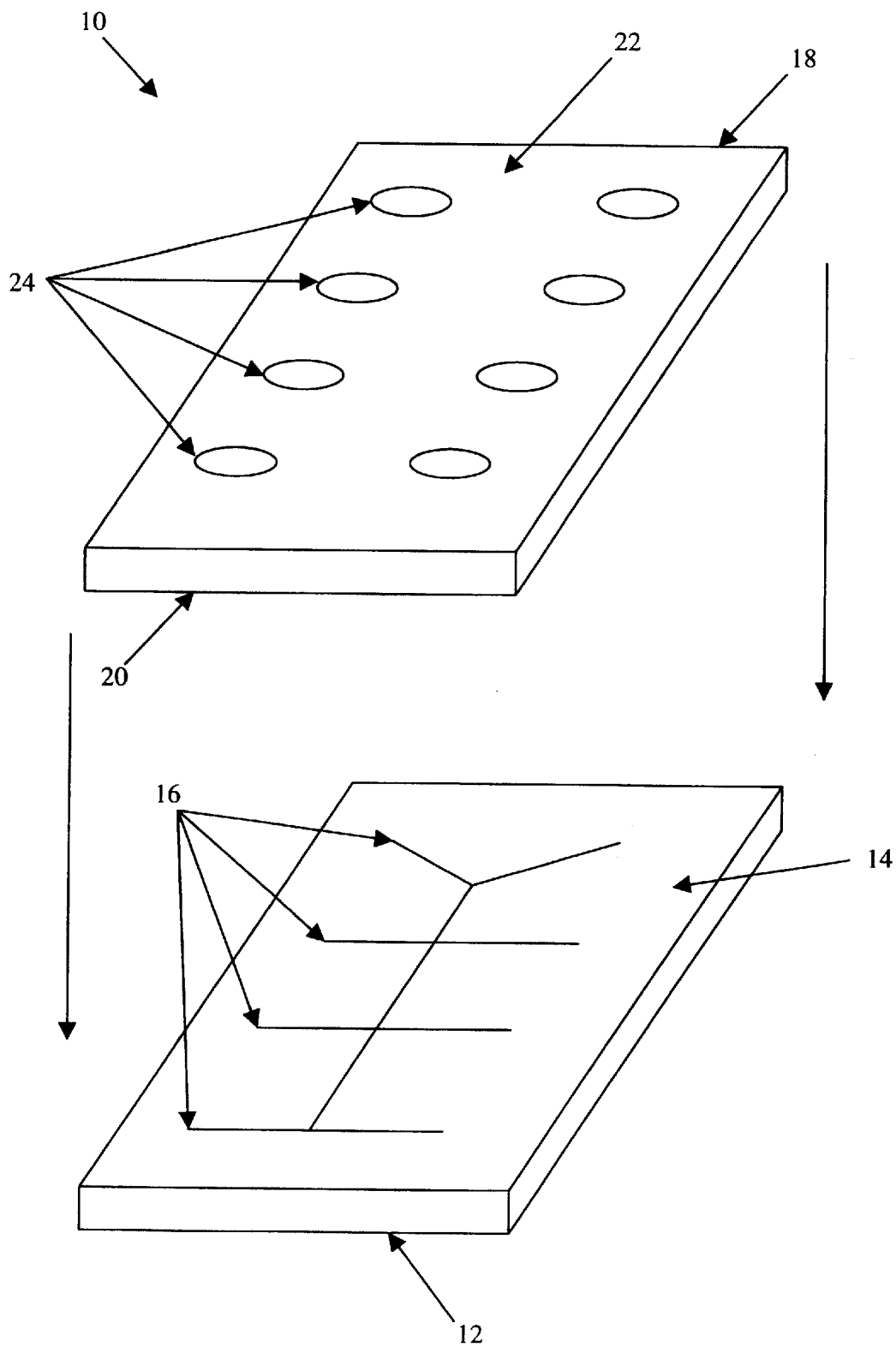
FIG. 1 illustrates the fabrication of a typical microfluidic device incorporating a multilayer fabrication strategy.

FIG. 1 illustrates a two layer body structure 10, for a microfluidic device. In preferred aspects, the bottom portion of the device 12 comprises a solid substrate that is substantially planar in structure, and which has at least one substantially flat upper surface 14. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. Pat. 5,885,470, and which is incorporated herein by reference in its entirety for all purposes.

The channels and/or chambers of the microfluidic devices are typically fabricated into the upper surface of the bottom substrate or portion 12, as microscale grooves or indentations 16, using the above described microfabrication techniques. The top portion or substrate 18 also comprises a first planar surface 20, and a second surface 22 opposite the first planar surface 20. In the microfluidic devices prepared in accordance with the methods described herein, the top portion also includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. The holes 24 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

These devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis. Examples of such sample introduction systems are described in e.g., U.S. Pat. No. 6,045,056 and U.S. Pat. No. 5,880,071, and is hereby incorporated by reference in its entirety for all purposes.

Microfluidic systems have been employed in the separation of biological macromolecules, in the performance of assays, e.g., enzyme assays, immunoassays, receptor binding assays, and other assays in screening for affectors of biochemical systems. Generally, such systems employ microscale channels and/or chambers through which various reactants are transported, where they may be mixed with additional reactants, subjected to changes in temperature, pH, ionic concentration, etc., separated into constituent elements and/or detected.

The result of the performance of these functions is often greatly affected by the rate at which the reactants are transported within the microscale channels of these microfluidic devices. In particular, the rate at which materials flow within these systems directly affects a number of parameters upon which the outcome of the reaction depends, at least in part. For example, where two reactants are being transported from separate channels into a common channel or chamber for reaction and subsequent detection, the flow rate of two reactants into the common channel affects the concentration of each reagent. Further, the rate at which the mixed reactants are transported to the detection region of the device affects the amount of time the mixed reagents are allowed to react, thereby directly affecting the amount of reaction product.

In microfluidic systems that employ pressure driven systems, e.g., external pressure sources, integrated micropumps and the like, the flow rate of fluids within a given channel is directly related to the viscosity of the fluid, the amount of pressure applied to the system, and the dimensions of the channel. While these parameters remains constant, the flow rate will also remain constant. As such, in these pressure driven systems, flow rates can be easily and accurately determined, either experimentally, or based upon well known physical principles.

In electrokinetically driven microfluidic systems, e.g., systems employing electrokinetic material transport systems, however, a number of additional factors can affect the flow rate of fluids within the channels of the device. As with pressure driven systems, where all of these factors can be maintained as a constant, flow rate will also remain constant. Unfortunately, however, in a large number of applications for which it is desired to use these microfluidic systems, maintaining all of these factors constant is not reasonably practicable. As such, it is highly desirable to be able to monitor and control flow rates in microfluidic systems employing these electrokinetic material transport systems.

As used herein, "electrokinetic material transport systems" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

Such electrokinetic material transport and direction systems include those systems hat rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode. "Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquoting, and the like. Similarly, downstream operations may include similar operations, including, e.g., separation of sample components, labeling of components, assays and detection operations. Assay and detection operations include without limitation, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like.

The systems described herein generally include microfluidic devices, as described above, in conjunction with additional instrumentation for controlling fluid transport and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format. A variety of controlling instrumentation may be utilized in conjunction with the microfluidic devices described above, for controlling the transport and direction of fluids and/or materials within the devices of the present invention. As noted above, the systems described herein preferably utilize electrokinetic material direction and transport systems. As such, the controller systems for use in conjunction with the microfluidic devices typically include an electrical power supply and circuitry for concurrently delivering appropriate voltages to a plurality of electrodes that are placed in electrical contact with the fluids contained within the microfluidic devices. Examples of particularly preferred electrical controllers include those described in, e.g., International Publication WO 98/00707, filed Jul. 3, 1997, the disclosures of which are hereby incorporated herein by reference in their entirety for all purposes. In brief, the controller uses electric current control in the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system. This current control is less susceptible to dimensional variations in the process of creating the microfluidic system in the device itself. Current control permits far easier operations for pumping, valving, dispensing, mixing and concentrating subject materials and buffer fluids in a complex microfluidic system. Current control is also preferred for moderating undesired temperature effects within the channels.

In the microfluidic systems described herein, a variety of detection methods and systems may be employed, depending upon the specific operation that is being performed by the system. Often, a microfluidic system will employ multiple different detection systems for monitoring the output of the system. Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, filed diameter, and focal length may be readily utilized as at least a portion of this optical train. The light detectors may be photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to the computer (described in greater detail below), via an AD/DA converter, for transmitting detected light data to the computer for analysis, storage and data manipulation.

In the case of fluorescent materials, the detector will typically include a light source which produces light at an appropriate wavelength for activating the fluorescent material, as well as optics for directing the light source through the detection window to the material contained in the channel or chamber. The light source may be any number of light sources that provides the appropriate wavelength, including lasers, laser diodes and LEDs. Other light sources may be required for other detection systems. For example, broad band light sources are typically used in light scattering/transmissivity detection schemes, and the like. Typically, light selection parameters are well known to those of skill in the art. The detector may exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer. As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an AD/DA converter as needed).

The computer typically includes appropriate software for receiving user instructions, either in the form of user input into a set parameter fields, e.g., in a GUI ("graphical user interface"), or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

II. Flow Monitoring and Control

As noted above, a number of factors can affect the flow rate of materials under the above-described electrokinetic material transport systems. For example, protein adsorption on channel surfaces can block charged groups on the surfaces of channels, which charged groups effect electrokinetic fluid movement. As such, in microfluidic systems which involve protein transport, such protein adsorption can result in reduced flow rates over the time of use of the device. Furthermore, the need for charged surface groups in electrokinetic systems generally prevents the use of surface treatments to prevent protein adsorption to these surfaces. The problems of protein adsorption are compounded in systems wherein protein containing fluids are only transported in one or a subset of the interconnected channels of the device. Specifically, protein adsorption in a subset of all channels of a system can result in variations in the flow rates of these channels whereas flow rates in other channels may be unaffected. As noted previously, variations in the relative flow rates of interconnected channels can result in variations of combination rates of materials from different channels, e.g., in performing dilutions, reactant addition and the like.

In addition, factors which affect the level of voltage drop across the length of the microscale channels of these microfluidic devices, will also affect the efficacy with which electrokinetic systems are able to manipulate fluids. Such factors include, e.g., the pH and/or ionic concentration of the fluid within the channels. In particular, lower ionic strength fluids will have a greater voltage drop per unit channel length than higher ionic strength fluids, resulting in a greater flow rate in electrokinetic systems. As a result, variations in buffer conditions, either from one assay system to another, or within the context of a single assay system, can result in a wide variation in electrokinetic flow rates in microfluidic channels from device to device, as well as among the channels of a single device.

Furthermore, in many applications or uses of microfluidic systems, the ultimate user, rather than the system manufacturer, will supply many of the fluids used in the device, e.g., in the form of samples or test compounds that are sought to be analyzed within the system. In such cases, these fluids may have widely varying compositions, ionic strengths, pH, and the like, which will affect flow rates in microfluidic systems.

The present invention addresses these problems by providing an in situ method for monitoring and controlling flow rates within a microfluidic system, in order to maintain the flow rates of the system at desired, e.g., constant, levels. In particular, the methods described herein employ an internal flow standard which permits the real time monitoring of flow rates within the channels of a microfluidic device, and in preferred aspects, within each separate channel of such devices. Further, the systems provided herein provide for the automated monitoring and control of those flow rates.

Generally, the methods and systems described herein, employ a source of a detectable signal, e.g., a signaling compound or composition, in fluid communication with a microfluidic channel in which the flow rate is to be monitored. A small, but detectable amount of the signal is injected into the channel in which the flow rate is to be determined, typically utilizing one of the electrokinetic injection schemes described above, e.g., pinched or gated injection. The amount of time for that signal to travel a predefined length of the channel is then determined and the flow rate is calculated.

In some embodiments, the signals used in the methods and systems described herein are already provided as an integral part of the operation being performed by the device. For example, where a microfluidic device is used to monitor the level of binding between a receptor and a ligand, e.g., in screening for inhibitors or enhancers of that interaction, one element, either the receptor or the ligand, typically has a detectable label incorporated into its structure or otherwise associated therewith, i.e., fluorescent, chromophoric, chromogenic, chemiluminescent, radioactive, etc. As such, a small amount of the labeled component of the particular operation or reaction may be separately injected as the signal into the microscale channel in which it is desired to determine the flow rate. Typically, the amount of such material injected will be only sufficiently large to permit detection. Limiting the amount of the labeled component that is injected serves to prevent or minimize any changes in flow rate which could potentially result from that labeled component. Typically, the injection of such material solely for the purpose of determining the flow rate within a given channel are maintained at volumes that are less than 10 nl, preferably, less than 1 nl, optimally less than 100 pl, and often, between about 1 pl and about 10 pl.

In alternative embodiments, a separate source of a signal is provided from which a small but detectable amount of signal is injected into the channel of interest. Typically, such sources are provided as separate fluid reservoirs that are in fluid communication with the channels of interest, typically via an appropriate channel.

As used herein, the term "signal" generally refers to a detectable property which can be transported along a microfluidic channel at the same, or at some readily calculable proportion of the flow rate of fluid within that channel. Typically, such signals comprise a detectable compound or composition, but may also comprise properties that are not, per se, a property of a particular compound or composition being transported, e.g., variations in temperature, optical or electrical properties, not necessarily associated with a single composition, e.g., such properties may result from the interface or interaction of one compound or composition with another. Generally, it is preferred to use signals that have little or no net electrophoretic mobility in the relevant pH, e.g., are substantially uncharged at the pH of the particular operation being performed by the device/system. Such materials are then capable of flowing at the flow rate of the bulk electroosmotic fluid flow within the channel. This obviates any need for providing a correction factor in the flow rate calculation to account for any electrophoretic biasing of the signal element during transport.

Typically, the signals used in accordance with the present invention are compounds or compositions which bear a detectable labeling group or moiety. In particularly preferred aspects, such detectable labeling groups are capable of producing an optically detectable signal. Such compounds include, e.g., fluorescent compounds, chemiluminescent compounds, chromophoric or chromogenic compounds, and colloidal compounds, e.g., compounds having visually detectable particles, e.g., gold, platinum, iron, and the like, associated therewith. These signals are readily detected using an appropriate optical detector positioned to take optical measurements from the channel of interest.

A number of non-optically detectable signals are optionally employed. Such nonoptical signals include compositions which have variations in pH, ionic strength, or which incorporate radiolabels, and the like. For example, the signal, e.g., the detectable compound or composition, may include a discrete volume of fluid having a varied pH or ionic strength over that of the remainder of fluid within the channels. Such a signal is readily detected by incorporating a pH or conductivity sensor within the channel. In the case of pH or ionic strength signals, as described herein, it will be appreciated that amounts of such signals injected into the microscale channels under electrokinetic systems must be sufficiently small so as to not substantially affect the flow rate that is sought to be determined. Typically, this is accomplished by injecting the detectable signal using a pinched injection scheme, such that only the amount of signal disposed in the channel intersection is injected into the channel, and which typically maintains the injected volume below 100 pI.

Once the signal is injected into the channel of interest, the amount of time required for that signal to travel a given distance in the channel is determined. In the simplest embodiments, the distance is the distance from the injection intersection to the detection window of the device, and the time required is the time from the injection to the moment that the detector registers the signal. However, in some embodiments, multiple detectors are provided at different points in the channel of interest or at different points in the microfluidic system, and the flow rate is determined from the time required for the signal to travel from one detector to the other. In intersecting channel structures, this allows one to use a single injected signal plug, routed through multiple channels, to determine flow rate in each of those channels, provided that each channel includes its own detector or pair of detectors.

In some cases, the signaling element may be provided that is readily distinguishable from the signal produced by the overall operation. For example, where the overall operation employs an optical signaling mechanism, e.g., fluorescence, a non-optical signaling mechanism is used for determination of flow rates, permitting distinction between the signals. Alternatively, optically detectable signals may be used in both the overall operation and the determination of flow rate, where those optical signals are distinguishable, e.g., fluorescent compounds which emit light at two different wavelengths, e.g., fluorescein and rhodamine. A wide variety of fluorescent dyes having varied fluorescence emission spectra are readily available from e.g., Molecular Probes, Inc.. This latter scheme permits the use of a single detection system for monitoring the overall reaction as well as monitoring flow rates. Specifically, an optical detector such as a laser activated fluorescence microscope employing dual wavelength detection optics, can separately detect fluorescent signals at each of the two different wavelengths, e.g., through the incorporation of dichroic optics and dual detectors.

Utilization of a flow rate signal that is distinguishable from the signal of the overall operation also permits the monitoring and determination of flow rates in a microfluidic system without significantly interrupting the performance of the overall operation the device, e.g., assay. This provides more accurate and useful "real-time" data regarding flow rates within the channels of the device. Further, such systems are readily used to inject periodic flow rate signals into the running system. This provides constant feedback of the flow rate in the system. In particular, regularly injected signaling compounds provide a regular detectable signal profile. Deviations in the flow rate of the system will result in deviations from this regular signal output, allowing correction by adjusting the voltage gradients applied to the system.

Flow rate monitoring systems are also provided for monitoring flow rates in multiple channels within a single device. In such cases, each of the separate channels will typically be in fluid communication with a source of labeled compound or detectable signal. Each channel will also typically include a detector disposed in communication with the channel, e.g., optical or sensory communication, at a given distance from the point at which the source of signal is in communication with that channel.

In many cases, the distance traveled is the distance from the point of injection of the signal, e.g., the point at which the source of signal compound is in fluid communication with the channel of interest, e.g., the intersection of the signal channel and the channel of interest, to a detection window disposed across the channel of interest. This method allows one to practice the present invention in the context of an unmodified microfluidic device, e.g., which does not include separate detection elements for determining flow rates. Alternatively, two discrete detection elements may be provided within a single channel a known distance apart. The flow rate is then calculated by determining the amount of time required for the signal to traverse that known distance. For more complex operations, more complex monitoring systems could be readily provided. For example, in complex channel networks, employing large numbers of intersecting channels, it is often desirable to determine the flow rates in each of several different channels. As such, separate flow rate monitoring elements or detectors may be placed in communication, e.g., optical or physical communication, with each channel in which flow rate information is desired.

II. Devices and Systems

Figure 2:
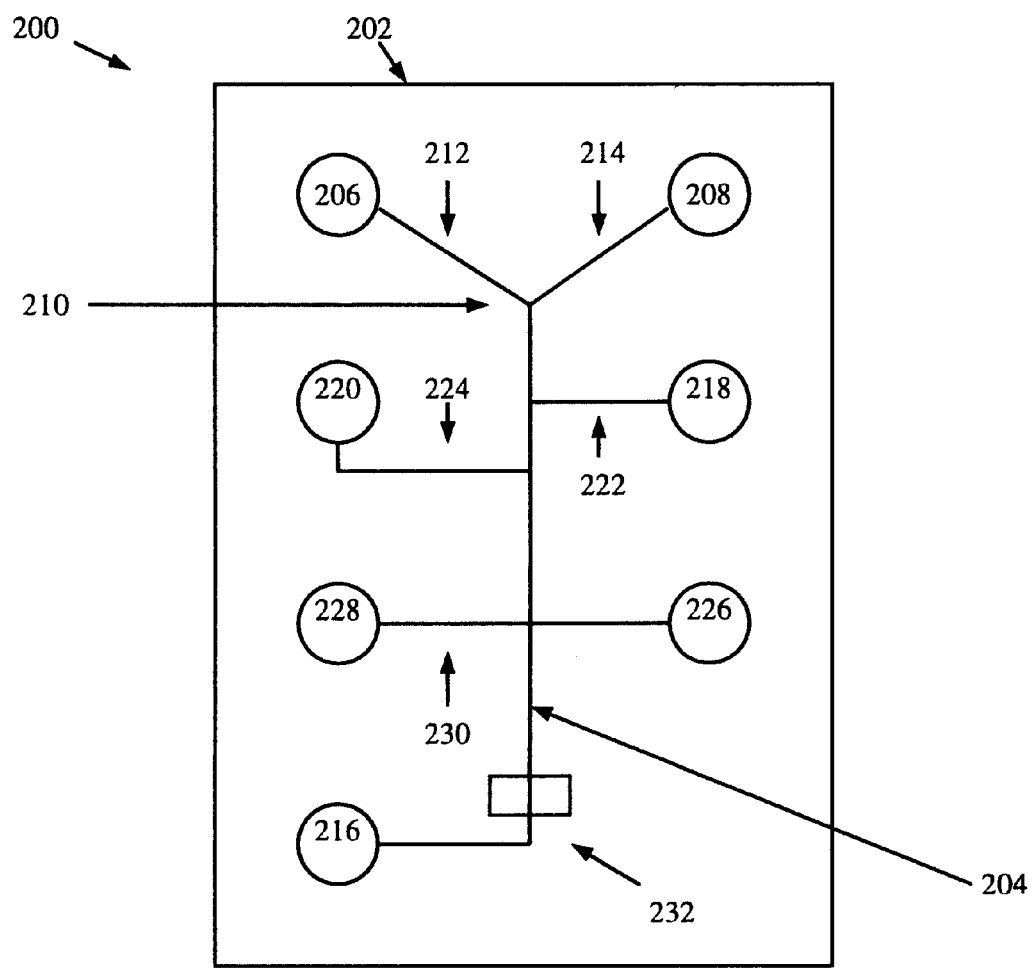
FIG. 2 illustrates a microfluidic device useful in practicing the methods of the present invention.

As noted above, the methods of monitoring flow rates according to the present invention can often be practiced in the context of the operation for which a particular device was intended, without the need for modifying the device. For example, FIG. 2 shows a typical microfluidic device that is utilized in performing a standard competitive diagnostic immunoassay, e.g., where the amount of a given antigen in a serum sample is determined based upon the ability of the serum to compete with a labeled antigen for binding to a supplied amount of antibody. As shown the microfluidic device 200 includes a body structure 202 having a main channel 204 disposed within the body structure. Serum reservoir 206 and a first buffer reservoir 208 are shown in fluid communication with one terminus of main channel 204 at channel intersection 210, via connecting channels 212 and 214, respectively. The opposite terminus of main channel 204 is in fluid communication with second waste reservoir 216. Labeled antigen and antibody are provided in reservoirs 218 and 220, respectively, which are in fluid communication with main channel 204 via connecting channels 222 and 224, respectively. A second buffer reservoir 226 and second waste reservoir 228 are provided at opposite termini of gating channel 230, which intersects and crosses main channel 204.

In performing the immunoassay, serum is transported from reservoir 206, to main channel 204. This serum is optionally diluted by a concurrent flow of buffer from reservoir 208 to main channel 204. At the same time, labeled antigen is transported from reservoir 218 to main channel 204 via connecting channel 222 where it mixes with the serum. Antibody is then transported from reservoir 220 to main channel 204, via channel 224 where it mixes with the serum/labeled antigen mixture. The transport of these materials from their respective reservoirs to the main channel, is carried out by applying an appropriate voltage gradient between reservoirs 206, 208, 218 , 220 and first waste reservoir 228, causing the materials in each of these reservoirs to flow toward waste reservoir 228. A gating or constraining flow of fluid is provided from buffer reservoir 226 to second waste reservoir 216, in order to control flow at the intersection of channel 230, and main channel 204. Periodic injections of the serum/antibody/antigen mixtures are then made into the remaining portion of main channel 204, whereupon the labeled antigen:antibody complex is separated from unbound labeled antigen, and detection by a detector disposed adjacent to a detection window 232 disposed across main channel 204 just prior to its turn toward second waste reservoir 216.

In a first option, the flow rate within the main channel may be determined by pumping the labeled antigen into first waste reservoir 228 while a constraining or gating flow of buffer is transported from buffer reservoir 226, to second waste reservoir 216. At time zero, the flow is switched such that the labeled antigen is transported toward second waste reservoir 216. The time required for the label front to reach the detection point is then determined and used to calculate the flow rate based upon the channel distance between the injection intersection and the detection window. A second and preferred option for determining flow rates in the main channel is to inject an extremely small but detectable amount of the labeled antigen into the main channel, and determine the time required for that amount of label to reach the detection window. By injecting only a small amount of labeled antigen, any effects of the antigen on the flow rate are minimized. Typically, very small quantities of the labeled antigen can be readily injected using the microfluidic systems described above. In particular, injection schemes are readily achieved for injecting volumes that are less than 1 nl, preferably less than 100 pl and often in the range of from about 10 to about 50 pl.

More complex comparative analyses of flow rates are also performed using the device and system shown in FIG. 2. For example, a dilution series of the labeled marker, e.g., the labeled antigen, is transported along main channel past the detection window. The dilution series is carried out by transporting successively larger proportions of buffer into the main channel from either of buffer reservoirs 208 or 226. In the electrokinetic systems, this is accomplished by applying a constant voltage gradient between both reservoirs 208 and 218, and second waste reservoir 216, e.g., the sum of the voltage gradient between reservoir 218 and waste reservoir 216 and reservoir 228 and waste reservoir 216 remains constant. During the dilution however, the voltage gradient contributed by the buffer or diluent and labeled marker reservoirs 208 and 218, respectively, is varied proportionally with the dilution steps desired.

Figure 5A:
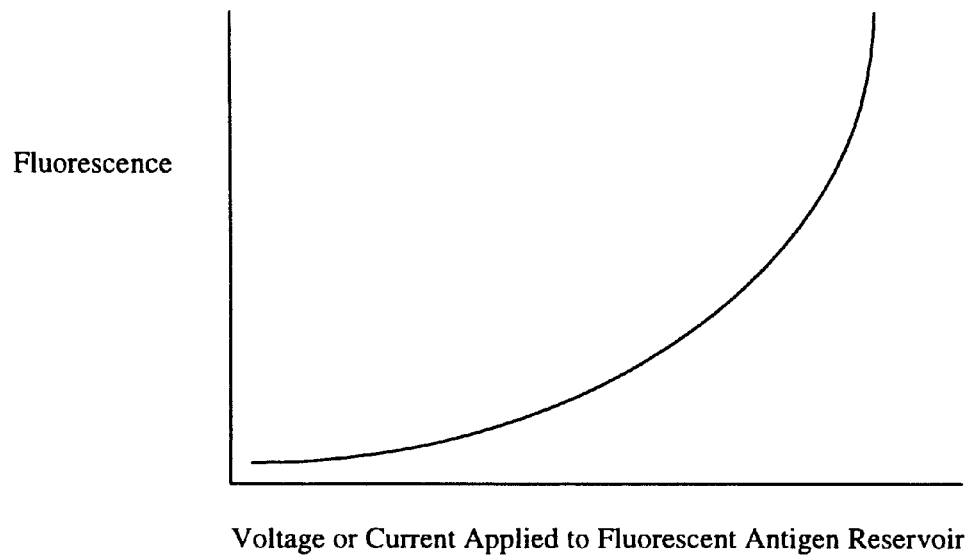
FIGS. 5A and 5B show plots of fluorescence vs. voltage or current applied to a fluorescent signal reservoir during a dilution series, for identifying variations in flow rates.
Figure 5B:
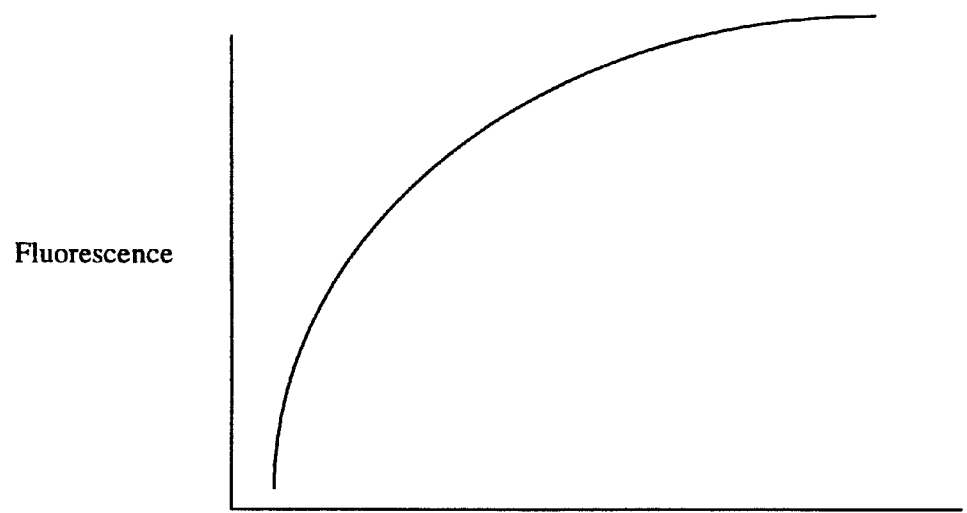

If, based upon the applied voltages, the flow rates in the labeled antigen channel and the diluent or buffer channel are equal, then the dilution series will provide a linear output of detectable label vs. voltage or current applied to the detectable antigen reservoir. However, where these flow rates are different based upon the applied voltage gradients, the dilution series will provide a curved output of fluorescence as a function of voltage gradient applied to transport the labeled antigen. Where the detectable signal (antigen) stream has a higher relative flow rate than the nondetectable stream (buffer), the output curve for the dilution series will have the general shape shown in FIG. 5A. Where the detectable stream has a slower relative flow rate than the nondetectable stream, the output curve for the dilution series will have the general shape shown in FIG. 5B. The curvature of the plot can also be used to readily calculate the relative flow rates of fluids coming from each channel which can, in turn, be used to control the relative flow rates.

In alternative, more complex aspects, as described above, additional reservoirs can be provided in fluid communication with any of the channels of the device, which reservoirs include a detectable signaling compound or composition. Small amounts of detectable signal are then injected into each channel and detected at a point in the channel that is removed from the injection point such that a flow rate can be calculated.

Figure 3:
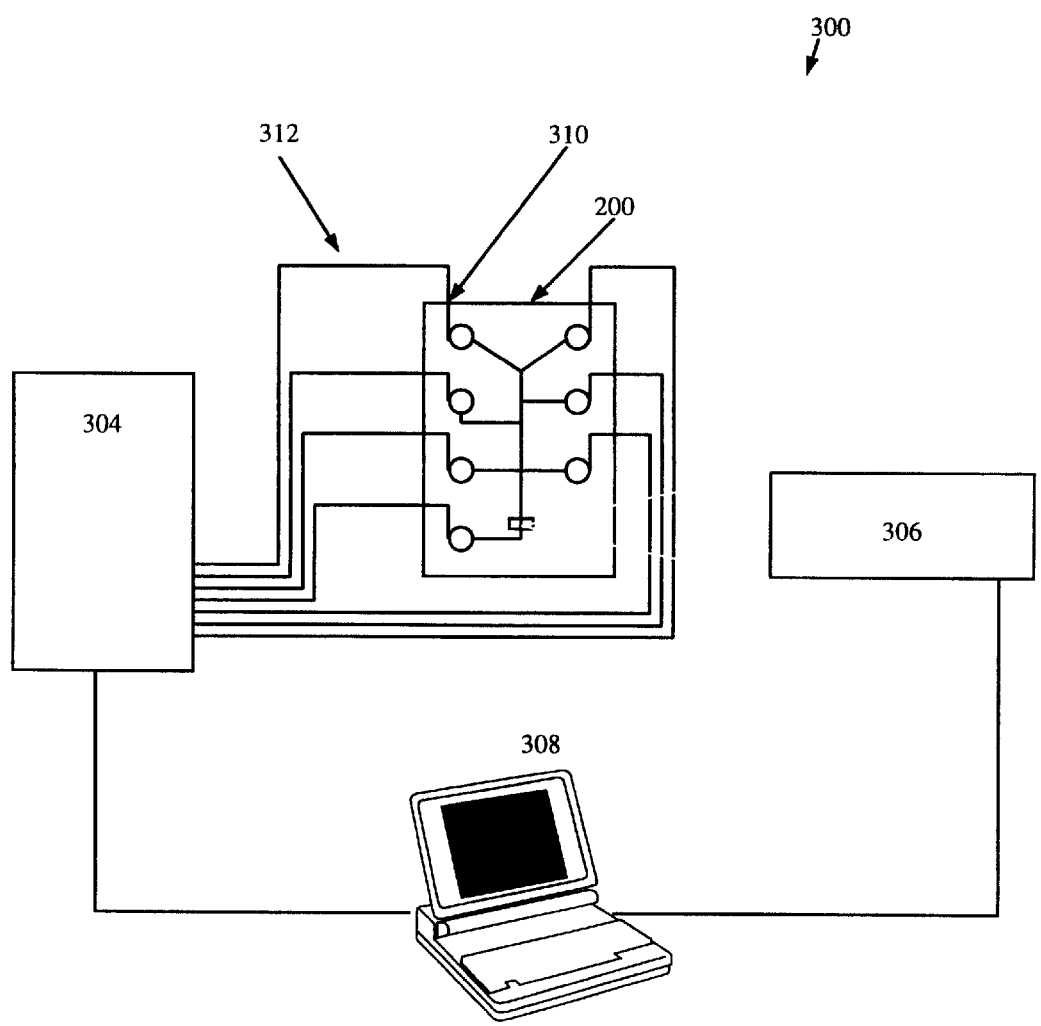
FIG. 3 illustrates an overall view of a control and monitoring system in accordance the present invention.

FIG. 3 illustrates an overall microfluidic system capable of utilizing the monitoring and control methods and systems of the present invention. As shown, the system 300 includes a microfluidic device, such as microfluidic device 200, shown in FIG. 2, an electrical controller 304, a detector 306 and a computer or other processor unit 308.

As shown, the microfluidic device includes one or more channels, such as channels 204, 212, 214, 222, 224 and 230 (as shown in FIG. 2) having a plurality of reservoirs or ports disposed at and in electrical contact with the termini of these channels, such as ports 206, 208, 216, 218, 220, 226 and 228 (as shown in FIG. 2).

An electrode 310 is placed in electrical contact with each of the ports, and is electrical coupled to controller 304 via electrical line 312. Appropriate voltages are delivered through lines 312 to the electrodes 310, in accordance with a flow profile desired for the given operation being performed by the system. Detector 306 is disposed adjacent the microfluidic device, and particularly disposed adjacent to the detection window 232, whereby the detector is capable of sensing a signal within that portion of the main channel 204 across which the detection window is disposed.

The computer portion of the system 308 is capable of performing a number of functions in the context of the overall microfluidic system, generally, and specifically with respect to the monitoring and control methods described herein. Specifically, the computer typically includes appropriate programming for instructing the application of voltages to the channel termini by the voltage controller 304, in order to carry out a desired fluid transport profile, which is either input by the user, or is contained in a separate program. Additionally, the computer receives data transmitted from the detector, and is typically appropriately programmed to store this data, as well as manipulate the data to provide an output that is readily comprehended by the user. In accordance with the present invention, the computer typically includes appropriate programming for monitoring and controlling flow rates within the microfluidic device. Such programming is optionally embodied in software stored in an appropriate memory device, such as a compact disk read only memory ("CDROMs"), hard disks, floppy disks, high capacity disks (e.g., ZipDrive™ available from Iomega), field programmable gate arrays ("FPGAs") electrically erasable programmable read only memories ("EEPROMs"), read only memories ("ROMs"), random access memories ("RAMs"), and the like.

In particular, the computer instructs the voltage controller to apply an appropriate voltage gradient across the length of the main channel, as discussed above, with reference to FIG. 2, to provide fluid flow in that channel. The computer then instructs the voltage controller to apply appropriate voltages to the ports to inject a small volume of the signaling compound into the main channel at time 0. The computer then receives the data from the detector indicating that the signal has traversed the detection window. From these data, the computer then calculates the actual flow rate of fluid within main channel 204, and compares this flow rate to an expected or desired flow rate, e.g., a set point as input by the user, or as set in an initial flow rate determination step. If the computer determines that the actual flow rate is less than the expected or desired flow rate, the computer increases the voltage gradient applied across the main channel and retests the flow rate. If, however, the actual flow rate is greater than the desired flow rate, the computer decreases the voltage gradient applied across the main channel. The size of the increase or decrease may be a small incremental increase or decrease, or may be an increase or decrease calculated from the size of the original voltage gradient and the actual flow rate.

Figure 4:
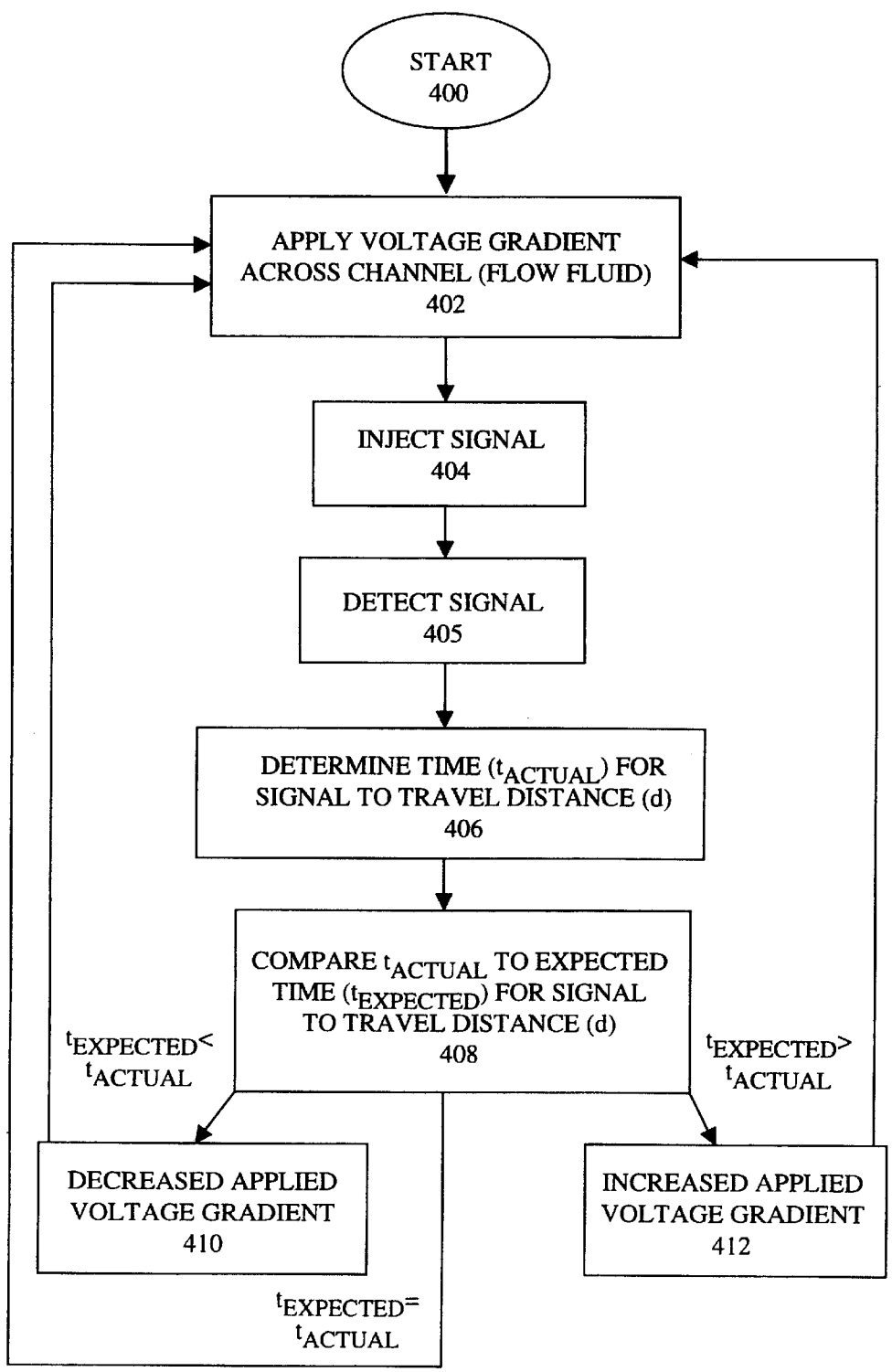
FIG. 4 is a flow chart illustrating process steps carried out by the control system and control software, in accordance with the present invention.

An example of process steps dictated by appropriate software programming are shown in FIG. 4. Briefly, the process is initiated at step 400. The computer instructs the voltage controller at step 402, to commence fluid flow in the channel in which a flow rate determination is desired, by applying a first voltage gradient across the length of the channel. At step 404, the computer instructs the system to inject a small amount of signal into the main channel by appropriate modulation of the applied voltages at the various ports of the device, as described previously. The signal is then detected as it passes the detection point at step 405, e.g., typically by a sensor device, such as an optical or potentiometric detector, which is operably linked to the computer. The time required ($t_{actual}$) for the signal to travel from the injection point to the detection point or window (the distance "d") is then determined at step 406. At step 408, this time is then compared with the expected time for the signal to travel distance "d" ($t_{expected}$). In alternative aspects, the computer optionally compares any of a variety of parameters, e.g., calculated flow rates, signal strengths, signal periodicity, etc., which can be used as measures of flow rate.

Where $t_{expected}$ is less than $t_{actual}$ the computer proceeds to step 410, whereupon the computer instructs the voltage controller to decrease the voltage gradient applied across the main channel, to decrease the actual flow rate. If however, $t_{expected}$ is greater than $t_{actual}$, then the computer proceeds to step 412, whereupon it instructs the computer to increase the voltage gradient applied across the length of the main channel. After performing one of steps 410 or 412, or in the case where the actual and expected times or flow rates are equal, the computer then repeats steps 404 through 414, to continuously monitor the flow rate, or verify the changes made to the voltage gradient/flow rates.

Although the present invention has been described in some detail by way of illustration and example for purposes of clarity and understanding, it will be apparent that certain changes and modifications may be practiced within the scope of the appended claims. All publications, patents and patent applications referenced herein are hereby incorporated by reference in their entirety for all purposes as if each such publication, patent or patent application had been individually indicated to be incorporated by reference.

What is claimed is:

1. A device or system for monitoring flow of a fluid in at least two channels, the device or system comprising:
   a body structure having at least first and second intersecting microscale channels disposed therein, wherein the first channel is fluidly coupled to a source of at least a first signaling composition and the second channel is fluidly coupled to the source of the at least first signaling composition or to a source of at least a second signaling composition;
   a flow controller for applying a pressure or voltage gradient in the first and second channels;
   one or more computers or processors operably coupled to the controller, the one or more computers or processors comprising an instruction set which directs the controller to flow a detectable amount of the at least first signaling composition from the source of the at least first signaling composition into the first channel during operation of the device, and for flowing the at least first signaling composition or the second signaling composition into the second channel; and
   one or more detectors proximal to the first or second channel, which one or more detectors are configured to detect the at least first or second signaling composition in the first or second channels, the detectors operably coupled to the one or more computers or processors, which computers or processors comprise an instruction set for determining the flow rate of the at least first signaling composition in the first channel and for determining the flow rate of the at least second signaling composition in the first channel.

2. The device or system of claim 1, wherein the first or second signaling composition comprises an optically detectable signal.

3. The device or system of claim 1, wherein the first or second signaling composition comprises a chemiluminescent, fluorescent, chromophoric or colloidal composition.

4. The device or system of claim 1, wherein the first signaling composition comprises fluorescein and the second signaling composition comprises rhodamine.

5. The device or system of claim 1, the detectable signaling composition comprising a zero net charge at a pH of a first fluid in the first channel.

6. The device or system of claim 1, therein the first signaling composition is different than the second signaling composition.

7. The device or system of claim 1, wherein the first or second signaling composition produces a light emission, and the detector comprises a light detector.

8. The device or system of claim 1, wherein the detector comprises a photodiode.

9. The device or system of claim 1, wherein the light detector comprises collection optics for transmitting a light emission incident on the collection optics to a photodiode.

10. The device or system of claim 1, wherein the detector comprises a source of excitation light at a sufficient wavelength for exciting the first or second signaling composition to produce a light emission, and optics which direct the excitation light through a detection window into the first channel.

11. The device or system of claim 1, further comprising an additional signaling composition in the first or second channel, which additional signaling composition produces a detectable signal that is different from the first or second detectable signal.

12. The device or system of claim 11, wherein the first, second and additional signaling compositions each comprise a different detectable label that emits or absorbs light, wherein the different detectable label on each of first, second and additional signaling compositions each emit or absorb light at a different wavelength.

13. The device or system of claim 1, comprising a detection window disposed on the first channel, the detection window being capable of transmitting a detectable signal from the first channel therethrough.

14. The device or system of claim 1, wherein the computer or processor comprises a time measurement element which measures a time interval between an initiation of flow of the first or second detectable signal into the first or second channel and detection of the first or second detectable signal by the detectors.

15. The device or system of claim 1, wherein the computer or processor receives signal data from the detector, calculates an actual flow rate of a fluid in the first channel from the signal data, compares the actual flow rate to a desired flow rate, and instructs the controller to modulate flow of the fluid in the first channel based upon a difference between the actual flow rate and the desired flow rate.

16. The device or system of claim 1, which computers or processors comprise an instruction set for increasing or decreasing flow in the first or second channel in response to the detected flow rate.

17. The device or system of claim 1, wherein the controller comprises a voltage regulation element for applying a voltage differential along the first or second channel.

18. The device or system of claim 1, wherein the controller comprises an electrical controller for concomitantly applying and modulating voltages at at least three reservoirs, which at least three reservoirs are fluidly coupled to the at least two channels, to flow a fluid in the first channel from a first reservoir to a second reservoir, and for periodically injecting a detectable amount of the signaling composition into the first channel from a third reservoir.

19. The device or system of claim 1, wherein the controller comprises a fluid pressure regulation element, which pressure regulation element applies positive or negative fluid pressure along the first or second channel.

20. The device or system of claim 1, further comprising a first fluid in the first channel, wherein the first signaling composition is injected into the first fluid in the first channel during flow of the first fluid in the first channel.

21. The device or system of claim 1, further comprising a first fluid in the first channel and a second fluid in the second channel, the first and second fluids being different, wherein the first signaling composition is injected into the first fluid in the first channel during flow of the first fluid in the first channel and wherein the first or second signaling composition is injected into the second fluid in the second channel during flow of the second fluid in the second channel.

22. The device or system of claim 1, further comprising a third channel disposed in the body structure, the third channel intersecting the first channel at a first terminus of the third channel and being fluidly coupled to a reservoir in fluid communication with a second terminus of the third channel.

\* \* \* \* \*

UNITED STATES PATENT AND TRADEMARK OFFICE
CERTIFICATE OF CORRECTION

PATENT NO. : 6,221,226 B1  Page 1 of 1
DATED : April 24, 2001
INVENTOR(S) : Kopf-Sill It is certified that error appears in the above-identified patent and that said Letters Patent is hereby corrected as shown below:

<u>Column 18,</u>
Line 17, please delete "therein" and insert -- wherein --.

Signed and Sealed this

Thirteenth Day of November, 2001

Attest:

*Attesting Officer*

NICHOLAS P. GODICI
*Acting Director of the United States Patent and Trademark Office*